(12) United States Patent
Watling et al.

(10) Patent No.: US 7,014,813 B1
(45) Date of Patent: Mar. 21, 2006

(54) METHODS AND APPARATUS FOR VAPOR PHASE STERILISATION

(75) Inventors: David Watling, Westcott (GB);
Anthony Michael Martin, Andover (GB)

(73) Assignee: Bioquell UK Limited, Andover Hampshire (GB)

( * ) Notice: Subject to any disclaimer, the term of this patent is extended or adjusted under 35 U.S.C. 154(b) by 785 days.

(21) Appl. No.: 10/088,595

(22) PCT Filed: Sep. 20, 2000

(86) PCT No.: PCT/GB00/03606

§ 371 (c)(1),
(2), (4) Date: Jun. 11, 2002

(87) PCT Pub. No.: WO01/21223

PCT Pub. Date: Mar. 29, 2001

(30) Foreign Application Priority Data

Sep. 21, 1999 (GB) .................................. 9922364

(51) Int. Cl.
*A61L 2/08* (2006.01)
(52) U.S. Cl. ........................... 422/26; 422/27; 422/28; 422/34; 422/120; 422/292; 422/305
(58) Field of Classification Search ............ 422/26–28, 422/30, 31, 34, 120, 292, 305
See application file for complete search history.

(56) References Cited

U.S. PATENT DOCUMENTS

| 4,512,951 A | 4/1985 | Koubek |
|---|---|---|
| 4,843,867 A | 7/1989 | Cummings |
| 4,898,713 A | 2/1990 | Picard |
| 4,992,247 A | 2/1991 | Foti |
| 5,173,258 A | 12/1992 | Childers |
| 5,785,934 A | 7/1998 | Jacobs et al. |
| 5,876,664 A * | 3/1999 | Childers et al. ............... 422/28 |
| 5,906,794 A | 5/1999 | Childers |

FOREIGN PATENT DOCUMENTS

| EP | 0 486 623 B1 | 1/1997 |
|---|---|---|
| EP | 0 774 263 A1 | 5/1997 |
| EP | 0 808 631 A1 | 11/1997 |
| GB | 2 217 619 A | 11/1989 |

(Continued)

OTHER PUBLICATIONS

P. Swartling et al., *The Sterilizing Effect Against Bacillus subtillis Spores of Hydrogen Peroxide at Different Temperatures and Concentrations*, J. Dairy Res. (1968), 35, 423, pp. 423-428.

(Continued)

*Primary Examiner*—David Redding
(74) *Attorney, Agent, or Firm*—Workman Nydegger

(57) ABSTRACT

An apparatus for sterilizing a sealable enclosure includes a circuit for flow of a sterilizing gas or gasses. The circuit is connected to the enclosure to be sterilized to form a closed circuit and pumps to circulate gas through the circuit and enclosure. The circuit has parallel branches one of which contains apparatus to deactivate a sterilant to be added to the carrier gas flowing through the circuit and apparatus to dehumidify the gas. The other branch contains apparatus to heat the gas and apparatus to supply a sterilant vapor or vapors to the gas. Control apparatus determines which of the parallel branches the gas flows through. The control apparatus maintains flow through one branch passage until the relative humidity falls below a predetermined level. The flow through that branch is then terminated and flow through the other branch initiated.

22 Claims, 2 Drawing Sheets

FOREIGN PATENT DOCUMENTS

| | | |
|---|---|---|
| GB | 2 308 066 A | 6/1997 |
| WO | WO 89/06140 | 7/1989 |
| WO | WO 91/05573 | 5/1991 |
| WO | WO 97/47331 | 12/1997 |
| WO | WO 98/57673 | 12/1998 |
| WO | WO 00/38745 | 7/2000 |

OTHER PUBLICATIONS

Walter C. Schumb et al, *Hydrogen Peroxide*, Reinhold Publishing Corporation, Chapter 8, pp. 447-448 (1968).

* cited by examiner

METHODS AND APPARATUS FOR VAPOR PHASE STERILISATION

BACKGROUND OF THE INVENTION

1. Field of the Invention

The present invention relates to methods and apparatus for sterilising the interior of a chamber using either a two component or a multi-component vapour, one component of which will be water.

2. Relevant Technology and Summary of the Invention

There are numerous applications for sterilising the interior of a chamber including its contents in the pharmaceutical, biotechnology, and food industries, as well as the medical world. A number of compounds have been used as sterilising agents some of which are only partially effective and some of which have serious side effects because they are toxic, corrosive, or can cause other environmental damage. Formaldehyde has long been used as a cheap and quite effective sterilising agent but doubts over its safety and environmental persistence may prevent continued use. Hydrogen peroxide is a simple and cheap compound with good sterilising properties. Its major advantage is that it can be decomposed to water and oxygen, which are totally harmless products. In the vapour phase, hydrogen peroxide can be used to treat work areas of size from safety cabinets to clean rooms. In all gas phase sterilisation, deep layers of contamination will not be effected and good cleaning procedures are necessary as a preliminary to gas phase sterilisation.

Hydrogen peroxide gas sterilisation and decontamination systems have been designed in order to avoid condensation, and as such both flow through and recirculating systems have been so organised as to keep the vapour concentrations, especially of water, below the dew point. Examples of such systems are described in EP-A-0486623B1, GB-B-2217619, WO89/06140 and GB-A-2308066.

More recent work has shown that for rapid surface sterilisation and decontamination in rooms and smaller chambers, or isolators, condensation of a mixture of vapours of a gaseous decontaminant such as hydrogen peroxide and water is essential. It is now believed that gaseous surface sterilisation using hydrogen peroxide is a condensation process so it would seem sensible to examine the process, to see how it may be optimised to take advantage of the condensation process. This knowledge may then be applied not only the sterilisation process using hydrogen peroxide gas but also other mixtures of sterilising gases that rely on condensation for their activity.

In the apparatus described in EP-A-0 486 623 B1 the air/gas mixture is circulated through the sealed chamber to be sterilised and then through the apparatus to produce and control the gas mixture. The gas returning to the apparatus is cleansed of any hydrogen peroxide gas and also dried before more water vapour and hydrogen peroxide gas are added. This cleansing and drying process is likely to be wasteful, as the vapours removed from the circulating gas must be replaced so that condensation may occur in the sealed chamber. The only reason for the removal of these vapours would be if the concentration of the hydrogen peroxide gas had been reduced because of decomposition.

It is now well understood that vapour phase decomposition does not occur at room temperatures, such homogenous decomposition only happens at elevated temperatures as reported in the paper "HYDROGEN PEROXIDE" by Walter C. Schumb, CHARLES N. SATTERFIELD, and RALPH L. WENTWORTH, published in AMERICAL CHEMICAL SOCIETY, MONOGRAPH SERIES, Catalog Card Number 55-7807, Chapter 8. Decomposition does however happen on surfaces, which are catalytic, but this appears to be very small amounts. To date no observer has seen a measurable increase in oxygen concentration, and the measured hydrogen peroxide gas concentrations conform very closely to the saturated vapour pressures of the original aqueous solution that is evaporated into the air stream. All of the indications are therefore that the amount of vapour phase decomposition of hydrogen peroxide is very small.

Since this sterilisation process relies on condensation of the hydrogen peroxide vapour then the most critical parameter is the rate at which this condensation may be achieved. The amount of hydrogen peroxide vapour available for condensation within the sealed enclosure will depend on the vapour concentration delivered to the chamber and the concentration leaving the chamber. The difference between these two amounts will be the quantity of hydrogen peroxide that is available to form a film of condensation.

The maximum concentration of vapour that can be delivered to the chamber depends on the temperature of the gas stream entering the chamber, the concentration of the aqueous sterilising solution being evaporated into the gas stream and the total water content of the gas. The carrier gas, normally air, that is used to transport the sterilising vapours through the total system will never be perfectly dry, even after passing through the drying system. This additional water in the carrier gas will dilute the hydrogen peroxide to a small extent and this additional water will reduce the amount of hydrogen peroxide that may be carried by the gas. The concentration of the vapour leaving the sealed chamber, once stable conditions have been reached, will be determined by the saturated vapour pressure for the conditions at the exit of the sealed chamber. Thus, if it is assumed that only insignificant amounts of decomposition occur, then the rate of condensation will depend on the concentration of the gases delivered to the chamber and the temperature of the gases leaving the chamber.

In general there are two factors that are important when considering a gaseous surface sterilisation process. The first and most important is to be sure that the process has been successful and the second is to achieve sterilisation in the minimum possible time. The most common technique for assuring sterility is to develop a cycle and to test the performance with biological indicators. This cycle development will include optimisation of each phase of the sterilisation cycle. This is a complex issue as there are many parameters to be considered during the optimisation process apart from the obvious considerations of gas concentration and flow. Some of the less obvious ones are the starting value of the relative humidity, the moisture content of any microorganism, the rate of condensation, and the length of time it may take for the condensate to kill any microorganism. The technique used for the removal of the sterilant gas at the end of the cycle will also have marked influence on the total cycle time.

The optimised cycle then becomes fixed using the same physical parameters such as flow rates, times etc., but does not take into account any external factors that may change, e.g. the external temperature which will have an influence on the effectiveness of the cycle.

The problem with this fixed technique is that if some external influences change which have not been taken into consideration during the cycle development then a cycle, although properly developed, may become unsuccessful. The best method to overcome this difficulty is to measure those parameters that actually cause the sterilisation and use these measurements to control the cycle, rather than to use a set of predetermined factors to run identical cycles. The technique of using the measurements to control the cycle will lead to changes in the details of the cycle to counteract any changes in the circumstances surrounding the process.

This procedure also has the advantage of ensuring the minimum reliable cycle time, since the process will progress to a point where it is effective and no further. It is not necessary to add large safety margins to the cycle to ensure that it is effective, as the point at which it is effective is known from the measurements.

The objects of the present invention are to control the sterilisation cycle using sensors, and to provide a recirculating system that does not require the steps of removing water vapour and sterilising gas mixtures during the critical sterilisation phase of the cycle.

U.S. Pat. No. 5,906,794 discloses a flow-through vapour phase sterilisation system which includes a sealable chamber with an inlet port and outlet port and a circuit fluidly connected to the chamber ports to provide a closed loop flow path for recirculating a carrier gas into through and out of the chamber. The system also includes a liquid sterilant vaporiser unit for delivering a vaporised liquid sterilant into the carrier gas flow upstream of the inlet port and a converter for converting the sterilant vapour to a form suitable for disposal is fluidly connected to the conduit circuit downstream of the chamber outlet port. A drying unit is included in the circuit downstream of the converter and has a valve for controlling flow to a first flow path through an air dryer and thence to the vaporiser or a second flow path which by passes the air dryer. By varying the amount of fluid through the first and second flow paths a selected portion of the carrier gas can be routed to by pass the dryer and the humidity of the carrier gas can be regulated to maintain a predetermined percent saturation sterilant vapour in the chamber as the sterilising cycle proceeds.

It is an object of the present invention to provide a sterilising system in which concentration of sterilant in the chamber to be sterilised is built up more rapidly to achieve condensation of sterilant in the chamber.

This invention provides a method of sterilising a sealable enclosure comprising the steps of circulating a carrier gas and sterilant through the enclosure and through a flow path having an outlet from the enclosure and an inlet to the enclosure, any sterilant in the gas flow received from the enclosure being rendered suitable for disposal, and the content of water vapour being reduced following which the gas flow is heated and further sterilant is added to sterilise the enclosure, wherein the flow path has two parallel branches in one of which any sterilant in the gas flow is rendered suitable for disposal and any water vapour content in the gas is reduced and in the other of which the carrier gas is heated and sterilant is added to the gas, the method further comprising the steps of initially circulating said carrier gas through said one branch, monitoring the moisture content of the gas in the enclosure and terminating flow of carrier gas through said one branch when the relative humidity in the enclosure has been reduced to a predetermined level such that the surfaces of the enclosure are relatively dry, initiating flow of the carrier gas through said other branch and adding a sterilant vapour or vapours to the gas passing through the other branch until condensation of the sterilant takes place in the enclosure, terminating supply of sterilant to the carrier gas, continuing to circulate the carrier gas substantially saturated with sterilant vapour for a predetermined time to ensure sterilisation of the enclosure terminating flow through said other branch and redirecting the flow of carrier gas through said one branch to extract the sterilant from the gas enclosure to render the sterilant suitable for disposal and to reduce the relative humidity of the carrier gas.

More specifically the invention provides a method of sterilising a sealable enclosure comprising the steps of initially reducing the relative humidity in the enclosure to about 30 to 40%, circulating a carrier gas to the enclosure, raising the temperature of the circulating gas above ambient, supplying a sterilant vapour or vapours to the circulating carrier gas sufficient to saturate substantially the gas whereby on cooling in the enclosure, a condensate of the sterilant vapour is formed on surfaces in the enclosure, distributing the gas/vapour throughout the enclosure to ensure that the condensate is formed on all surfaces in the enclosure, measuring the amount of condensate formed on a surface of the enclosure and continuing to circulate the gas/vapour until a required amount of condensate has formed in the enclosure terminating supply of sterilant vapour to the gas whilst continuing to circulate the saturated gas/vapour to maintain the condensate on the surface for a predetermined period of time and finally extracting the sterilant vapour from the carrier gas whilst continuing to circulate the carrier gas through the enclosure to extract the condensate from the enclosure.

Preferably the sterilant vapour is extracted from the carrier gas by breaking down the vapour into disposable constituents.

It is also preferred that the sterilant vapour is hydrogen peroxide and water vapour. In this case the hydrogen peroxide extracted from the chamber with the circulating gas is subjected to catalytic action to break the hydrogen peroxide down into water vapour and oxygen, the former being extracted from the gas before the gas is recirculated through the enclosure.

The initial step of reducing the relative humidity in the enclosure may be carried out by circulating the carrier gas through the chamber and extracting water vapour from the circulating gas outside the chamber.

The relative humidity in the enclosure may be reduced initially to about 35%. In addition, the enclosure may be held at said reduced relative humidity for a period of time according to the size of enclosure and flow rate of gas to ensure dryness of said surfaces in the enclosure.

Entry to one branch is closed and entry to the other branch may be opened and vice versa to provide flow through one or other of the branches. For example, valve means may permit flow into one branch and not the other and vice versa.

Alternatively, pump means may be provided in said parallel branches and are used to cause gas flow along one or other of the parallel branches in the flow path.

The invention further provides apparatus for sterilising a sealable enclosure comprising a circuit for flow of a gas or gasses, the circuit having means to receive and connect an enclosure to be sterilised in the circuit to form a closed circuit therewith, means to circulate gas through the circuit and enclosure, and having two parallel branches in the circuit one of which contains means to deactivate a sterilant to be added to the carrier gas flowing through the circuit and means to dehumidify the gas and the other of which branches contains means to heat the gas and means to supply a sterilant vapour or vapours to the gas, the apparatus further comprising control means for determining through which of the parallel branches the gas flows, the control means including means to determine the relative humidity of the gas exiting the enclosure and being operable to maintain flow through said one branch passage open until the relative humidity falls below a predetermined level and then to terminate flow through that branch and to initiate flow in the other branch and means to measure condensation in the enclosure to terminate flow in said other branch and to initiate flow in said one branch when the required amount of condensation has built up in the enclosure.

The apparatus may further include means to distribute the gas/vapours throughout the enclosure to ensure that the condensate is formed on all surfaces in the enclosure.

It has been found that in aqueous solutions of hydrogen peroxide very fast kill rates are achieved even at 10% hydrogen peroxide concentrations with even faster kills at 20% solution. Since we believe that gaseous surface sterilisation is a micro condensation process, then it may be considered to be analogous to the work "THE STERILISING EFFECT AGAINST BACILLUS SUBTILIS SPORES OF HYDROGEN PEROXIDE AT DIFFERENT TEMPERATURES AND CONCENTRATIONS;" by P. SWARTLING and B. LINDGREN J. DAIRY RES. (1968), 35,423. This gives a good guide as to the expected results that may be achieved with a gaseous condensation process.

This also suggests that should some small amount of decomposition occur because of surface catalysation of the gas then kills would still be achieved. In reality such decomposition appears to be very small indeed as indicated by the gas concentration data.

BRIEF DESCRIPTION OF THE DRAWINGS

The following is a description of some specific embodiments of the invention, reference being made to the accompanying drawings in which.

DETAILED DESCRIPTION OF THE PREFERRED EMBODIMENTS

Figure 1:
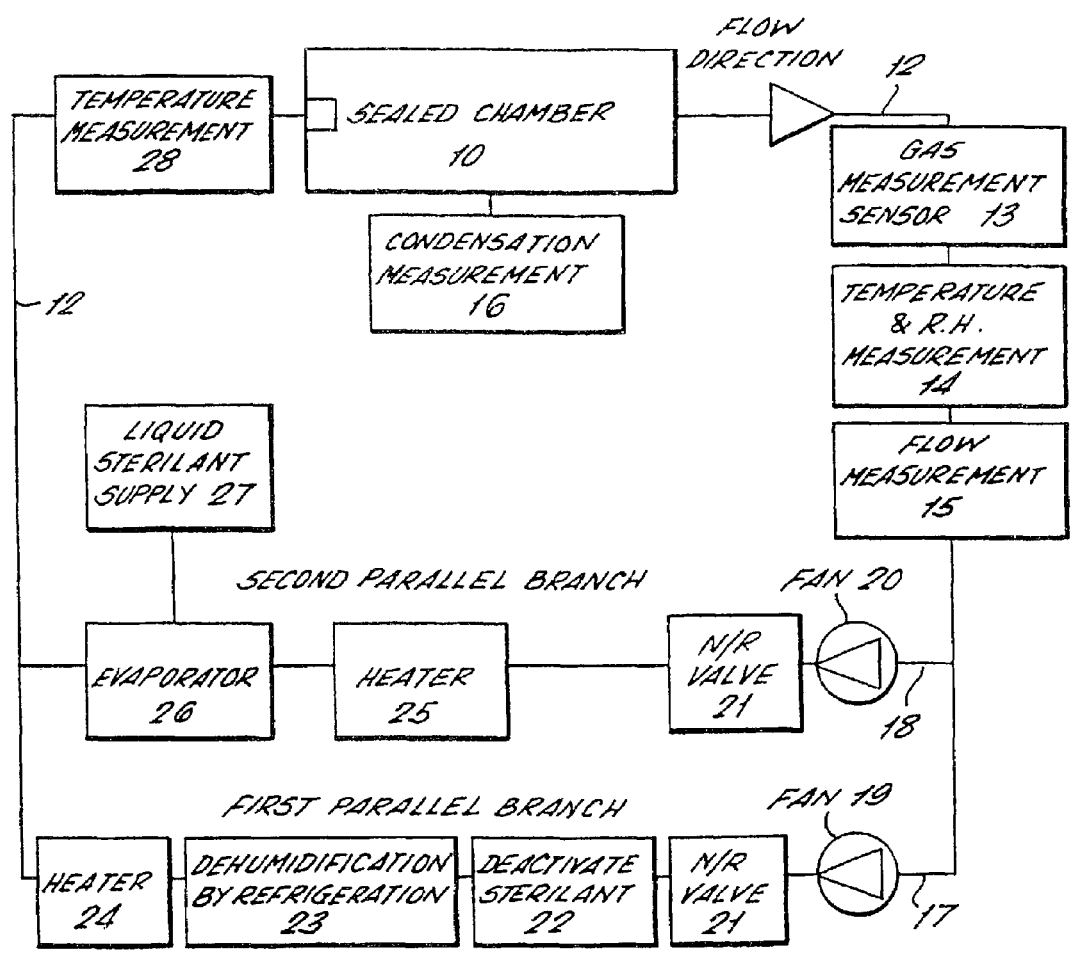
FIG. 1 is a diagrammatic view of a sealed chamber and a sterilisation circuit connected to the chamber for sterilising the interior and contents of the chamber using a gas carrying an aqueous vapour of a liquid sterilant, the circuit having two pumps or fans.

The apparatus comprises a sealed chamber 10, and an apparatus included generally at 11 incorporating a dual circuit for dehumidification, sterilising and aeration of the sealed chamber 10. A carrier gas, i.e. air, and a sterilising gas or gases are drawn from the sealed chamber to the apparatus through sealed connections fluidly connecting the chamber to the apparatus.

The apparatus comprises a gas flow circuit 12 containing in series, a gas monitor 13 a temperature and humidity monitor 14 and a flow measurement device 15. The gas monitor is an electrochemical cell giving a signal proportional to the gas concentration or can be a near infra-red spectrophotometer. Suitable temperature and humidity sensors 14 are commonly available as a single commercial instrument, and any such device that is resistant to hydrogen peroxide vapour would be suitable for this application. The most suitable, and cost effective, flow measurement 15 system is based on the measurement of the pressure difference across a restriction in the flow, typically an orifice plate.

Attached to the sealed chamber is a condensation measurement system 16. Proprietary systems are not readily available, but techniques have been developed that rely on the change in reflectivity of a surface in the chamber to indicate the mass of condensate that has formed. Alternative techniques that may include measuring equipment be mounted on the outside of the chamber.

Downstream of the flow measurement system the circuit divides into two parallel branches 17, 18. Each branch has a fan 18, 19 and each fan has an associated non-return valve 21. As the pressure required to force the circulating gas round the system is generally not large then a standard variable speed centrifugal fan would suffice for such an application. The non-return valves are required to ensure that there is no back flow in the wrong direction. Simple flap devices are all that is required in this application. In the first parallel branch 17 is a system 22 to deactivate and remove the sterilant gas or gases from the carrier gas, and a further system 23 to dehumidify the gas stream. Downstream of the dehumidification system is a heater 24 to raise the circulating gas temperature. The deactivating system for the sterilant gas comprises a catalyst bed, which decomposes the vapour to harmless components. For hydrogen peroxide gas a suitable catalyst would be ruthenium on inert pellets which decomposes the gas to water vapour and oxygen.

A desiccant dryer may perform the dehumidification process, but a more suitable technique would be to reduce the gas temperature using a refrigeration system. The reduction in temperature causes the water vapour to condense with the products of decomposition. The resulting condensate and decomposition products may then be pumped away. It is necessary to raise the circulating gas temperature after dehumidification and an electric heater 24 or other heating means is placed downstream of the dehumidifier for the purpose.

In the second parallel branch is a heater 25 to raise the gas temperature prior to entering an evaporator 26, in which the liquid sterilant is turned to vapour by heating. A liquid sterilant supply 27 controls the liquid flow to the evaporator.

The heater 25 may be of a similar construction to the other heater 24. The evaporator is a flash evaporator in which the liquid sterilant is evaporated by dropping under gravity a stream of liquid onto a heated surface. The flow of liquid from the sterilant supply is fed onto the heated surface at a selected rate by using a variable speed pump, which is controlled from a flow measuring system. The gas temperature entering the sealed chamber 10 is measured at 28 using a standard temperature probe. Gas entry to the chamber 10 is through a gas distribution system including a rotating nozzle arrangement which projects gas at high temperature and velocity to every part of the chamber. In addition a system for control gas pressure in the circuit to raise or reduce pressure as required is provided.

Figure 2:
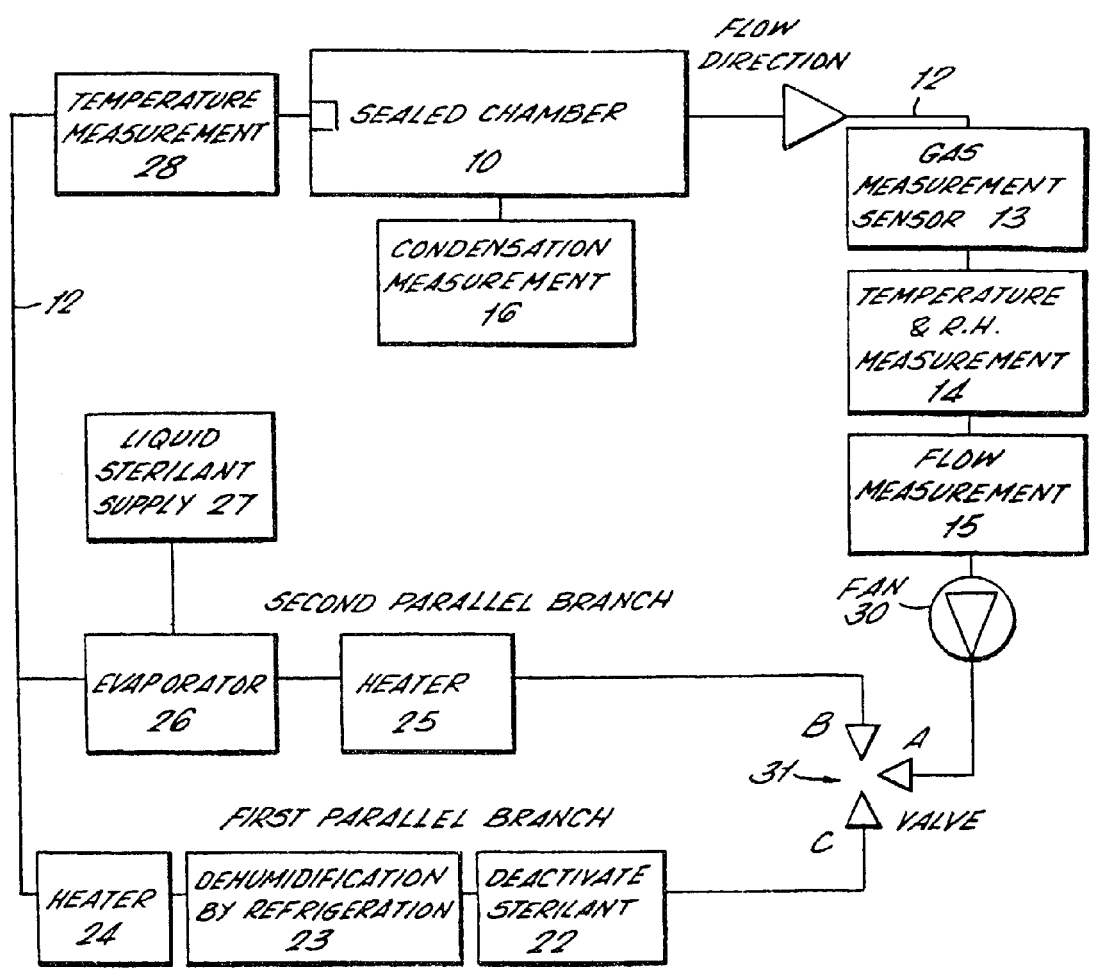
FIG. 2 is a diagrammatic view of a sealed chamber and a further form of circuit connected to the chamber for sterilisation of the interior of the chamber and its contents using a gas containing an aqueous vapour of a liquid sterilant, the circuit having a single pump or fan.

The components in the alternative arrangement shown in FIG. 2 are the same, with the same numbering except for the fan and valve arrangement. In FIG. 2 the gas or gases are driven round the system by a single fan of pump 30. The gas or gas mixtures leaving the fan or pump pass to a three way valve 31, which diverts the flow either to the first parallel branch by connecting port A to port C, or to the second parallel branch by connecting port A to port B. The valve is typically an electrically driven three-way ball valve.

The method of sterilising the enclosure using the above apparatus comprises the steps or reducing the relative humidity in the enclosure, then circulating a carrier gas containing an aqueous vapour of the sterilising gas or gases, and finally removing the sterilising gas or gases.

The first phase of reducing the relative humidity is essential to ensure that all of the surfaces inside the sealable chamber are at the same state of dryness. During the second phase the sterilising gas or gases are delivered to the sealed chamber at an elevated temperature in order that as much as possible of the sterilant may be transported into the sealed chamber. The third and final stage is the removal of the sterilant gas or gases by passing clean dry carrier gas into the sealed chamber to carry away the active gas or gases.

The first phase of reducing the humidity may be in two parts, the first to reduce the relative humidity to a pre-selected value, and a second part to hold the humidity at that value to allow the sealed chamber to come to a stable state.

Similarly the second phase when the gas or gases are passed into the sealed chamber is in two parts. The first part is to raise the concentration and generate the required level of condensation on the surfaces, with a second dwell part to allow the condensate to act on the microorganisms. The level of condensation is measured during the first part of the second phase and when it has reached the required level the supply of sterilising gas or gases is stopped but the carrier gas with the associated saturated vapours continues to circulate. The circulating saturated vapour prevents evaporation of the layer of condensation allowing the liquid film to act on the microorganisms.

During the third and final phase of the sterilisation cycle the carrier gas together with the sterilising gas or gases is circulated through a system to render the active gases harmless, so that it may be taken away, whilst at the same time removing the water vapour in a dehumidifier. The clean carrier gas is then returned to the sealed chamber where it gathers more of the active gas or gases thus further reducing to the level of the active ingredients. This process continues until the amount of active ingredients have been reduced to an acceptable level.

1. The relative humidity (RH) must be controlled at the start of the sterilisation cycle. We have established that the optimum value is between 30 and 40%. There are two points to be considered about the starting value of RH, the first is to obtain the shortest possible cycle (this requires the RH to be reduced to about 35%), and the second is to achieve a repeatable cycle. The repeatability depends on using the same starting value of RH and this may well have to be higher than 35% depending on local conditions. As it may not always be practical to achieve a starting value of 35% for the RH then it is essential that the same starting value is always used. Higher values of RH will increase the time required to achieve sterilisation as the condensate forming on surfaces will be diluted by any water that is present.
2. The amount of condensation is important; it too much is formed, the time to remove the surface layer after sterilisation has been achieved will be increased, as it would take longer to dry the surfaces. If insufficient condensation is allowed to form then sterilisation will not take place. The accurate measurement of this surface layer is essential to the process.
3. From the work of Swartling et al referred to above, it is clear that some "soaking" time will be required for the condensed liquid to be effective. This is built into the sterilisation cycle as a dwell period, a safety margin should be allowed within this dwell period to ensure that a total kill has been achieved. This period will normally be no more than a few minutes including the safety margin.
4. The distribution of the hot gas entering the chamber is also important. As the gas enters the chamber it will rapidly start to cool and form condensation. If the gas is not thoroughly mixed as it enters the chamber then there will be sites of preferential condensation. If this should happen then it follows that other areas within the chamber will have less condensation, and to achieve a total kill in all areas an excess of gas will be required. This excess will be unevenly distributed and also take longer to remove at the end of the cycle when it is required to return the chamber to normal use.
5. The measurement of the concentration and temperature of the gas leaving the chamber tells the system that saturated vapour pressure has been reached. Whilst this is not a critical parameter it does indicate that condensation will form. If the concentration is too low and condensation does not form then the cycle should be aborted and these measurements will confirm that action.

Thus the process cycle comprises the following steps:
1. The chamber is brought to a starting value of RH, normally 35%. The chamber should be held at this level for a few minutes to ensure all of the surfaces have been brought to equilibrium.
2. Sterilising gas or gases and water vapour are passed into the chamber at an elevated temperature and distributed so as to generate an even layer of condensation. The amount of condensation is measured and when it has reached a sufficient value the gas and water vapour generator is switched off.
3. The condensed gas or gases and water remain on the surfaces for a sufficient length of time to cause sterilisation.
4. At the end of the dwell period the chamber is fed with clean dry air, which causes the surface condensation to evaporate and is therefore cleared from the chamber.

What is claimed is:

1. A method of sterilizing a sealable enclosure comprising:
    circulating a carrier gas and sterilant through the enclosure and through a flow path having an outlet from the enclosure and an inlet to the enclosure, any sterilant in the gas flow received from the enclosure being rendered suitable for disposal, and the content of water vapor being reduced following which the gas flow is heated and further sterilant is added to sterilize the enclosure, the flow path having two parallel branches in one of which any sterilant in the gas flow is rendered suitable for disposal and any water vapor content in the gas is reduced and in the other of which the carrier gas is heated and sterilant is added to the gas;
    initially circulating said carrier gas through said one branch, monitoring the moisture content of the gas in the enclosure and terminating flow of carrier gas through said one branch when the relative humidity in the enclosure has been reduced to a predetermined level such that the surfaces of the enclosure are relatively dry;
    initiating flow of the carrier gas through said other branch and adding a sterilant vapor or vapors to the gas passing through the other branch until condensation of the sterilant takes place in the enclosure;
    terminating supply of sterilant to the carrier gas; and
    continuing to circulate the carrier gas substantially saturated with sterilant vapor for a predetermined time through the other branch and enclosure to ensure sterilization of the enclosure terminating flow through said other branch and redirecting the flow of carrier gas through said one branch to extract the sterilant from the gas enclosure to render the sterilant suitable for disposal and to reduce the relative humidity of the carrier gas.

2. A method as claimed in claim 1, wherein entry to one branch is closed and entry to the other branch is opened and vice versa to provide flow through one or other of the branches.

3. A method as claimed in claim 2, wherein a valve permits flow into one branch and not the other and visa versa.

4. A method as claimed in claim 2, wherein a pump is used in the flow path to circulate said carrier gas.

5. A method as claimed in claim 2, wherein a pump is provided in said parallel branches and is used to cause gas flow along one or other of the parallel branches in the flow path.

6. A method as claimed in claim 1, wherein water vapor is removed from the gas in said one branch by cooling the gas to cause the water vapor to condense, the resulting condensate being removed.

7. A method as claimed in claim 6, wherein the gas cooled in said one branch is heated following said cooling step.

8. A method as claimed in claim 1, further comprising:
   initially reducing the relative humidity in the enclosure to about 30 to 40%;
   circulating a carrier gas to the enclosure;
   raising the temperature of the circulating gas above ambient;
   supplying a sterilant vapor or vapors to the circulating carrier gas sufficient to saturate substantially the gas, whereby on cooling in the enclosure, a condensate of the sterilant vapor is formed on surface in the enclosure;
   distributing the gas/vapor throughout the enclosure to ensure that the condensate is formed on all surfaces in the enclosure;
   measuring the amount of condensate formed on a surface of the enclosure and continuing to circulate the gas/vapor until a required amount of condensate has formed in the enclosure terminating supply of sterilant vapor to the gas whilst continuing to circulate the saturated gas/vapor to maintain the condensate on the surface for a predetermined period of time; and
   extracting the sterilant vapor from the carrier gas whilst continuing to circulate the carrier gas through the enclosure to extract the condensate from the enclosure.

9. A method as claimed in claim 8, wherein the sterilant vapor is extracted from the carrier gas by breaking down the vapor into disposable constituents.

10. A method as claimed in claim 8, wherein the sterilant vapor is hydrogen peroxide and water vapor.

11. A method as claimed in claim 10, wherein the hydrogen peroxide extracted from the chamber with the circulating gas is subjected to catalytic action to break the hydrogen peroxide down into water vapor and oxygen, the former being extracted from the gas before the gas is recirculated through the enclosure.

12. A method as claimed in claim 8, wherein the initial step of reducing the relative humidity in the enclosure is carried out by circulating the carrier gas through the chamber and extracting water vapor from the circulating gas outside the chamber.

13. A method as claimed in claim 8, wherein the relative humidity in the enclosure is reduced to about 35%.

14. A method as claimed in claim 8, wherein the enclosure is held at said reduced relative humidity for a period of time according to the size of the enclosure and flow rate of gas to ensure dryness of said surfaces in the enclosure.

15. A method as claimed in claim 8, wherein the condensate is maintained on the surfaces within the enclosure for a predetermined period to ensure sterilization of the surfaces.

16. An apparatus for sterilizing a sealable enclosure comprising:
   a circuit for flow of a gas or gasses, the circuit comprising:
      means for receiving and connecting an enclosure to be sterilized in the circuit to form a closed circuit therewith;
      means for circulating gas through the circuit and enclosure;
      two parallel branches in the circuit one of which contains means for deactivating a sterilant in the carrier gas flowing through the circuit and means for dehumidifying the gas but lacks means for adding sterilant and the other of said branches contains means for heating the gas and means for supplying a sterilant vapor or vapors to the gas;
   the apparatus further comprising control means for determining through which of the parallel branches the gas flows, the control means comprising:
      means for determining the relative humidity of the gas exiting the enclosure and being operable to maintain flow through said one branch passage open until the relative humidity falls below a predetermined level and then to terminate flow through that branch and to initiate flow in the other branch; and
      means for measuring condensation in the enclosure to terminate flow in said other branch and to initiate flow in said one branch when the required amount of condensation has built up in the enclosure.

17. An apparatus as claimed in claim 16, wherein the means for circulating gas further comprises
   a fan provided in the circuit between the enclosure and the parallel branches of the circuit to cause gas flow around the circuit; and
   means are provided at the entry to the first and second branches which are selectively operable for permitting flow through one or the other of the branches.

18. An apparatus as claimed in claim 16, wherein the means for circulating gas further comprises fans in both branches in the circuit which are selectively operable to cause flow of gas through one or other of the branches.

19. An apparatus as claimed in claim 16, further comprising means for distributing the gas/vapors throughout the enclosure to ensure that condensate is formed on all surfaces in the enclosure.

20. An apparatus as claimed in claim 16, wherein the means for deactivating the sterilant in said one branch comprise means for breaking the sterilant extracted from the enclosure down into disposable constituents.

21. An apparatus as claimed in claim 20, wherein the sterilant is hydrogen peroxide vapor and water vapor and the means for breaking the sterilant down comprise means for acting on the hydrogen peroxide to break the hydrogen peroxide down into water vapor and oxygen.

22. An apparatus as claimed in claim 16, wherein the means for lowering the relative humidity of the circulating carrier gas comprise means for cooling the gas to extract moisture therefrom by condensation and means for heating the gas above ambient following said condensation process.

* * * * *

UNITED STATES PATENT AND TRADEMARK OFFICE
CERTIFICATE OF CORRECTION

| | | |
|---|---|---|
| PATENT NO. | : 7,014,813 B1 | Page 1 of 4 |
| APPLICATION NO. | : 10/088595 | |
| DATED | : March 21, 2006 | |
| INVENTOR(S) | : Watling et al. | |

It is certified that error appears in the above-identified patent and that said Letters Patent is hereby corrected as shown below:

Drawings
Sheet 1, replace Figure 1 with the figure depicted herein below, in which the "apparatus" has been labeled with --11--

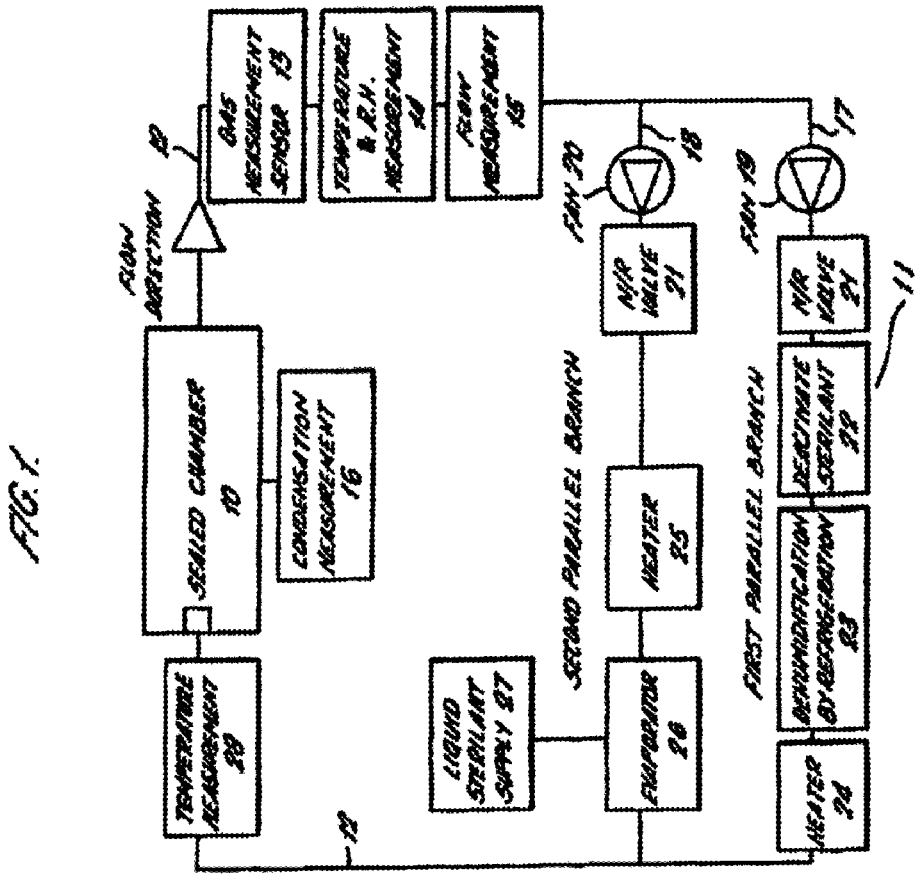

UNITED STATES PATENT AND TRADEMARK OFFICE
CERTIFICATE OF CORRECTION

PATENT NO.        : 7,014,813 B1
APPLICATION NO.   : 10/088595
DATED             : March 21, 2006
INVENTOR(S)       : Watling et al.

Page 2 of 4

It is certified that error appears in the above-identified patent and that said Letters Patent is hereby corrected as shown below:

Drawings
Sheet 2, replace Figure 2 with the figure depicted herein below, in which the "apparatus" has been labeled with --11--

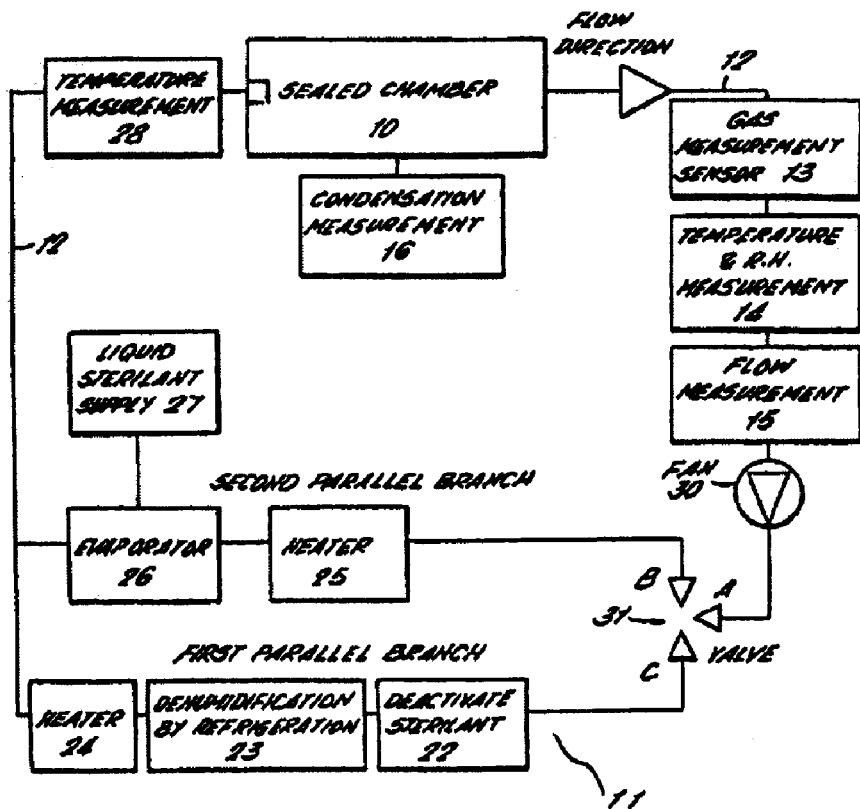

UNITED STATES PATENT AND TRADEMARK OFFICE
CERTIFICATE OF CORRECTION

PATENT NO.         : 7,014,813 B1
APPLICATION NO. : 10/088595
DATED                  : March 21, 2006
INVENTOR(S)       : Watling et al.

It is certified that error appears in the above-identified patent and that said Letters Patent is hereby corrected as shown below:

Column 1
Line 65, change "Walter C. Schumb" to --WALTER C. SCHUMB--

Column 2
Line 59, after "e.g." insert --,--

Column 3
Line 20, after "into" insert --,--
Line 23, after "port" insert --,--

Column 4
Line 45, after "or" insert --the--

Column 5
Line 53, after "13" --,--
Line 54, after "14" insert --,--

Column 6
Line 6, change "18, 19" to --19, 20--
Line 60, change "or" to --of--

Column 7
Line 28, remove [to]
Line 47, change "it" to --if--

UNITED STATES PATENT AND TRADEMARK OFFICE
CERTIFICATE OF CORRECTION

PATENT NO. : 7,014,813 B1
APPLICATION NO. : 10/088595
DATED : March 21, 2006
INVENTOR(S) : Watling et al.

It is certified that error appears in the above-identified patent and that said Letters Patent is hereby corrected as shown below:

Column 9
Line 6, change "visa" to --vice--

Signed and Sealed this

Fifth Day of February, 2008

JON W. DUDAS
*Director of the United States Patent and Trademark Office*

UNITED STATES PATENT AND TRADEMARK OFFICE
CERTIFICATE OF CORRECTION

| | | |
|---|---|---|
| PATENT NO. | : 7,014,813 B1 | Page 1 of 5 |
| APPLICATION NO. | : 10/088595 | |
| DATED | : March 21, 2006 | |
| INVENTOR(S) | : Watling et al. | |

It is certified that error appears in the above-identified patent and that said Letters Patent is hereby corrected as shown below:

Delete the title page and substitute therefor the attached title page.

Drawings
Sheet 1, replace Figure 1 with the figure depicted herein below, in which the "apparatus" has been labeled with --11--

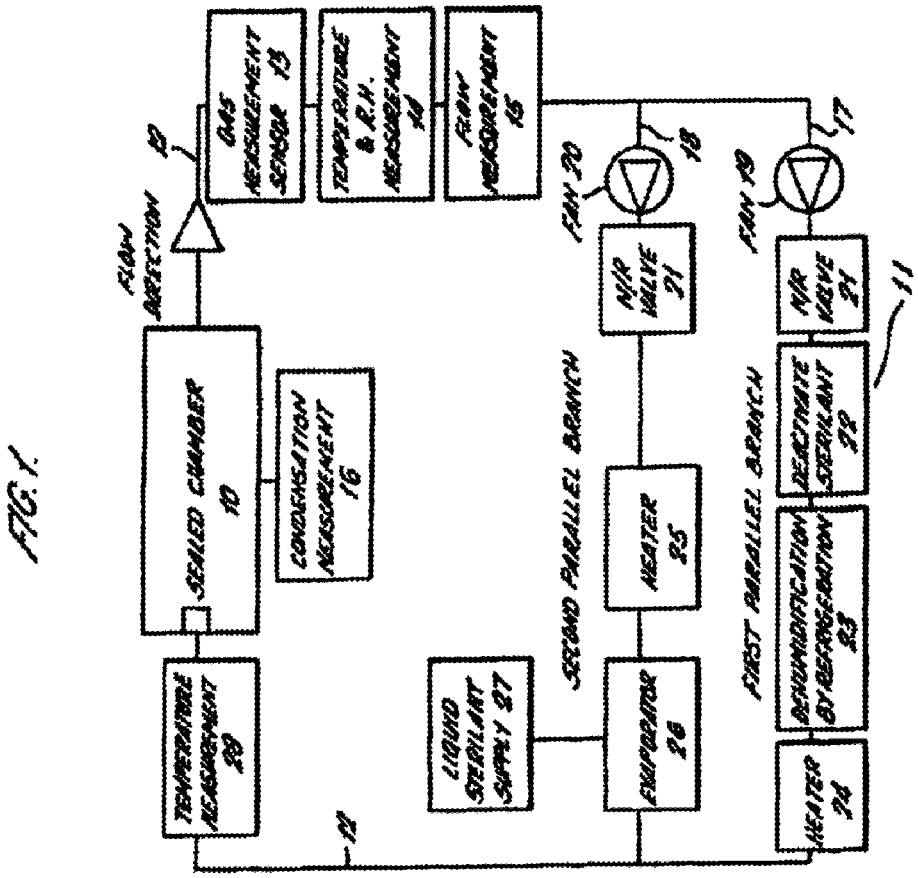

UNITED STATES PATENT AND TRADEMARK OFFICE
CERTIFICATE OF CORRECTION

PATENT NO.       : 7,014,813 B1
APPLICATION NO.  : 10/088595
DATED            : March 21, 2006
INVENTOR(S)      : Watling et al.

It is certified that error appears in the above-identified patent and that said Letters Patent is hereby corrected as shown below:

Drawings
Sheet 2, replace Figure 2 with the figure depicted herein below, in which the "apparatus" has been labeled with --11--

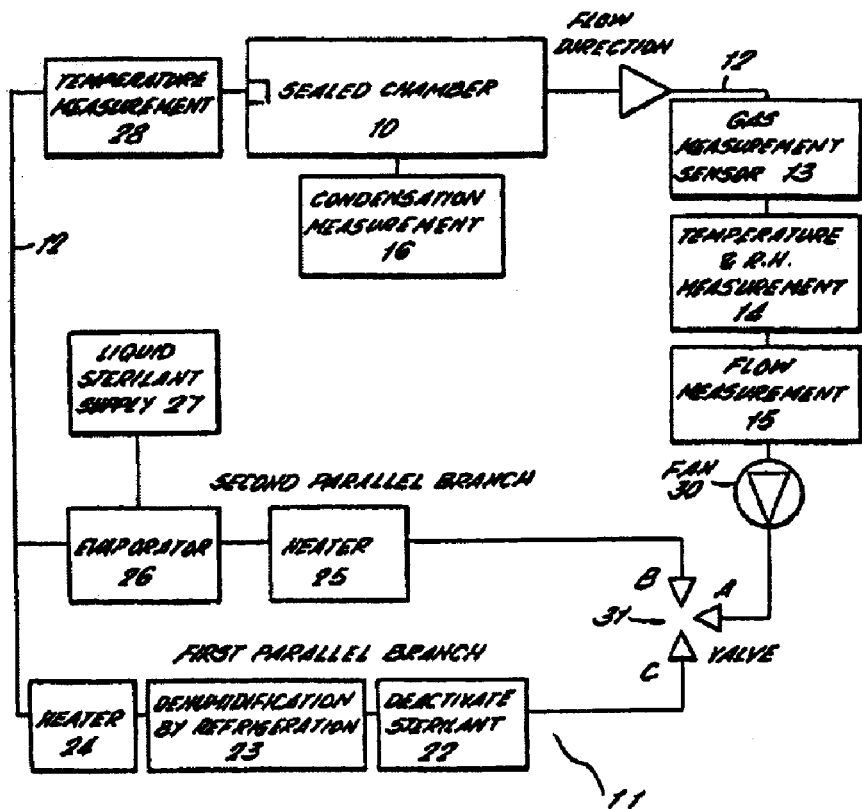

UNITED STATES PATENT AND TRADEMARK OFFICE
CERTIFICATE OF CORRECTION

| | |
|---|---|
| PATENT NO. | : 7,014,813 B1 |
| APPLICATION NO. | : 10/088595 |
| DATED | : March 21, 2006 |
| INVENTOR(S) | : Watling et al. |

It is certified that error appears in the above-identified patent and that said Letters Patent is hereby corrected as shown below:

Column 1
Line 65, change "Walter C. Schumb" to --WALTER C. SCHUMB--

Column 2
Line 59, after "e.g." insert --,--

Column 3
Line 20, after "into" insert --,--
Line 23, after "port" insert --,--

Column 4
Line 45, after "or" insert --the--

Column 5
Line 53, after "13" --,--
Line 54, after "14" insert --,--

Column 6
Line 6, change "18, 19" to --19, 20--
Line 60, change "or" to --of--

Column 7
Line 28, remove [to]
Line 47, change "it" to --if--

UNITED STATES PATENT AND TRADEMARK OFFICE
CERTIFICATE OF CORRECTION

PATENT NO. : 7,014,813 B1
APPLICATION NO. : 10/088595
DATED : March 21, 2006
INVENTOR(S) : Watling et al.

It is certified that error appears in the above-identified patent and that said Letters Patent is hereby corrected as shown below:

Column 9
Line 6, change "visa" to --vice--

This certificate supersedes the Certificate of Correction issued February 5, 2008.

Signed and Sealed this

Twenty-sixth Day of February, 2008

JON W. DUDAS
*Director of the United States Patent and Trademark Office*

United States Patent
Watling et al.

(10) Patent No.: US 7,014,813 B1
(45) Date of Patent: Mar. 21, 2006

(54) METHODS AND APPARATUS FOR VAPOR PHASE STERILISATION

(75) Inventors: David Watling, Westcott (GB); Anthony Michael Martin, Andover (GB)

(73) Assignee: Bioquell UK Limited, Andover Hampshire (GB)

(*) Notice: Subject to any disclaimer, the term of this patent is extended or adjusted under 35 U.S.C. 154(b) by 785 days.

(21) Appl. No.: 10/088,595

(22) PCT Filed: Sep. 20, 2000

(86) PCT No.: PCT/GB00/03606

§ 371 (c)(1),
(2), (4) Date: Jun. 11, 2002

(87) PCT Pub. No.: WO01/21223

PCT Pub. Date: Mar. 29, 2001

(30) Foreign Application Priority Data

Sep. 21, 1999 (GB) .................................. 9922364

(51) Int. Cl.
*A61L 2/08* (2006.01)

(52) U.S. Cl. .................. 422/26; 422/27; 422/28; 422/34; 422/120; 422/292; 422/305

(58) Field of Classification Search ........... 422/26–28, 422/30, 31, 34, 120, 292, 305
See application file for complete search history.

(56) References Cited

U.S. PATENT DOCUMENTS

| | | |
|---|---|---|
| 4,512,951 A | 4/1985 | Koubek |
| 4,843,867 A | 7/1989 | Cummings |
| 4,898,713 A | 2/1990 | Picard |
| 4,992,247 A | 2/1991 | Foti |
| 5,173,258 A | 12/1992 | Childers |
| 5,785,934 A | 7/1998 | Jacobs et al. |
| 5,876,664 A * | 3/1999 | Childers et al. ............ 422/28 |
| 5,906,794 A | 5/1999 | Childers |

FOREIGN PATENT DOCUMENTS

| | | |
|---|---|---|
| EP | 0 486 623 B1 | 1/1997 |
| EP | 0 774 263 A1 | 5/1997 |
| EP | 0 808 631 A1 | 11/1997 |
| GB | 2 217 619 A | 11/1989 |

(Continued)

OTHER PUBLICATIONS

P. Swartling et al., *The Sterilizing Effect Against Bacillus subtillis Spores of Hydrogen Peroxide at Different Temperatures and Concentrations*, J. Dairy Res. (1968), 35, 423, pp. 423-428.

(Continued)

*Primary Examiner*—David Redding
(74) *Attorney, Agent, or Firm*—Workman Nydegger

(57) ABSTRACT

An apparatus for sterilizing a sealable enclosure includes a circuit for flow of a sterilizing gas or gasses. The circuit is connected to the enclosure to be sterilized to form a closed circuit and pumps to circulate gas through the circuit and enclosure. The circuit has parallel branches one of which contains apparatus to deactivate a sterilant to be added to the carrier gas flowing through the circuit and apparatus to dehumidify the gas. The other branch contains apparatus to heat the gas and apparatus to supply a sterilant vapor or vapors to the gas. Control apparatus determines which of the parallel branches the gas flows through. The control apparatus maintains flow through one branch passage until the relative humidity falls below a predetermined level. The flow through that branch is then terminated and flow through the other branch initiated.

22 Claims, 2 Drawing Sheets